(12) United States Patent
Saul et al.

(10) Patent No.: US 6,875,192 B1
(45) Date of Patent: *Apr. 5, 2005

(54) DEVICES AND METHODS FOR REMOVING CEREBROSPINAL FLUIDS FROM A PATIENT'S CSF SPACE

(75) Inventors: Tom A. Saul, El Granada, CA (US); Marvin L. Sussman, Miami, FL (US)

(73) Assignee: Eunoe, Inc., Pleasanton, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 10/405,116

(22) Filed: Mar. 31, 2003

Related U.S. Application Data

(63) Continuation of application No. 10/138,082, filed on May 3, 2002, now Pat. No. 6,575,928, which is a continuation of application No. 09/189,037, filed on Nov. 10, 1998, now Pat. No. 6,383,159.

(51) Int. Cl.[7] .................................................. A61M 5/00
(52) U.S. Cl. ............................. 604/9; 604/8; 604/500; 604/264
(58) Field of Search ............................. 604/264, 8–10, 604/247, 500, 28, 30, 33

(56) References Cited

U.S. PATENT DOCUMENTS

| | | |
|---|---|---|
| 3,111,125 A | 11/1963 | Schulte |
| 3,886,948 A | 6/1975 | Hakim |
| 3,889,687 A | 6/1975 | Harris et al. |
| 3,913,587 A | 10/1975 | Newash |
| 3,985,140 A | 10/1976 | Harris |
| 4,156,422 A | 5/1979 | Hildebrandt et al. |
| 4,261,341 A | 4/1981 | Hakim et al. |
| 4,375,816 A | 3/1983 | Labianca |
| 4,377,169 A | 3/1983 | Banks |
| 4,385,636 A | 5/1983 | Cosman |

(Continued)

FOREIGN PATENT DOCUMENTS

| | | |
|---|---|---|
| EP | 115973 | 8/1984 |
| EP | 117695 | 9/1984 |
| EP | 421558 | 4/1991 |
| EP | 478842 | 4/1992 |
| EP | 798011 | 10/1997 |
| EP | 798012 | 10/1997 |
| FR | 2354103 | 1/1978 |
| FR | 5705574 | 5/1993 |

(Continued)

OTHER PUBLICATIONS

Barnett et al., "Normal pressure hydrocephalus in children and young adults" *Neurosurgery* (1987) 20(60):904–907.
Boon et al., "Does CSF outflow resistance predict the response to shunting in patients with normal pressure hydrocephalus?" *Acta Neurochir.* (1998) 71:331–333.

(Continued)

*Primary Examiner*—Manuel Mendez
(74) *Attorney, Agent, or Firm*—Townsend and Townsend and Crew LLP

(57) ABSTRACT

Devices and methods for removing cerebrospinal fluid (CSF) from a CSF space of a patient at relatively constant flow rates for patients having normal intracranial pressures, e.g. patients not suffering from hydrocephalus. The devices and methods provide drainage paths which permit the removal of CSF at relatively low flow rates, usually below, 0.2 ml/min, at normal intracranial pressures, e.g. an intracranial pressure between −170 mm of $H_2O$ in upright patients and 200 mm of $H_2O$ in reclining patients. The removal of CSF at relatively low, constant rates is particularly suitable for treating Alzheimer's disease and other conditions related to the presence of toxic and/or pathogenic substances in the CSF.

43 Claims, 7 Drawing Sheets

U.S. PATENT DOCUMENTS

| | | |
|---|---|---|
| 4,432,853 A | 2/1984 | Banks |
| 4,532,932 A | 8/1985 | Batty, Jr. |
| 4,540,400 A | 9/1985 | Hooven |
| 4,551,128 A | 11/1985 | Hakim et al. |
| 4,557,721 A | 12/1985 | Hooven |
| 4,560,375 A | 12/1985 | Schulte et al. |
| 4,576,035 A | 3/1986 | Hooven et al. |
| 4,595,390 A | 6/1986 | Hakim et al. |
| 4,598,579 A | 7/1986 | Cummings et al. |
| 4,601,724 A | 7/1986 | Hooven et al. |
| 4,605,395 A | 8/1986 | Rose et al. |
| 4,610,658 A | 9/1986 | Buchwald et al. |
| 4,627,832 A | 12/1986 | Hooven et al. |
| 4,631,051 A | 12/1986 | Harris |
| 4,673,384 A | 6/1987 | Marion |
| 4,675,003 A | 6/1987 | Hooven |
| 4,676,772 A | 6/1987 | Hooven |
| 4,681,559 A | 7/1987 | Hooven |
| 4,705,499 A | 11/1987 | Hooven |
| 4,714,458 A | 12/1987 | Hooven |
| 4,714,459 A | 12/1987 | Hooven |
| 4,729,762 A | 3/1988 | Doumenis |
| 4,741,730 A | 5/1988 | Dormandy, Jr. et al. |
| 4,769,002 A | 9/1988 | Hooven |
| 4,776,838 A | 10/1988 | Sainte-Rose et al. |
| 4,781,672 A | 11/1988 | Hooven |
| 4,787,886 A | 11/1988 | Cosman |
| 4,850,955 A | 7/1989 | Newkirk |
| 4,861,331 A | 8/1989 | East et al. |
| 4,867,740 A | 9/1989 | East |
| 4,931,039 A | 6/1990 | Coe et al. |
| 4,933,156 A | 6/1990 | Quay et al. |
| 4,950,232 A | 8/1990 | Ruzicka et al. |
| 5,039,511 A | 8/1991 | Quary et al. |
| 5,069,663 A | 12/1991 | Sussman |
| 5,167,615 A | 12/1992 | East et al. |
| 5,334,315 A | 8/1994 | Matkovich et al. |
| 5,336,166 A | 8/1994 | Sierra |
| 5,368,556 A | 11/1994 | Lecuyer |
| 5,385,541 A | 1/1995 | Kirsch et al. |
| 5,385,582 A | 1/1995 | Ommaya |
| 5,387,188 A | 2/1995 | Watson |
| 5,425,368 A | 6/1995 | Brandt |
| 5,437,627 A | 8/1995 | Lecuyer |
| 5,458,606 A | 10/1995 | Cohen et al. |
| 5,462,667 A | 10/1995 | Wollinsky et al. |
| 5,601,985 A | 2/1997 | Trojanowski et al. |
| 5,643,194 A | 7/1997 | Negre |
| 5,643,195 A | 7/1997 | Drevet et al. |
| 5,660,200 A | 8/1997 | Paes |
| 5,980,480 A | 11/1999 | Rubenstein et al. |
| 6,383,159 B1 | 5/2002 | Saul et al. |

FOREIGN PATENT DOCUMENTS

| | | |
|---|---|---|
| FR | 2685206 | 6/1993 |
| SE | 8801516 | 3/1987 |
| SU | 1297870 | 5/1989 |
| WO | WO 96/28200 | 9/1996 |
| WO | WO 98/02202 | 1/1998 |

OTHER PUBLICATIONS

Chapman et al., "The relationship between ventricular fluid pressure and body position in normal subjects and subjects with shunts: A telemetric study" Neurosurgery (1990) 26:181–189.

Condon et al., "A question index of ventricular and extra-ventricular intracranial CSF volumes using MR imaging" J. Comput. Assist. Tomogr. (1986) 10:784–792.

Condon et al., "MR relaxation times of cerebrospinal fluid" J. Comput. Assist. Tomogr. (1987) 11:203–207.

Czosnyka et al., "Posture–related overdrainage: Comparison of the performance of 10 hydrocephalus shunt in vitro" Neurosurgery (1998) 42(2):327–334.

Damasceno et al., "The predictive value of cerebrospinal fluid tap–test in normal pressure hydrocephalus" Arq. Neurosiquiatr. (1997) 55(2):179–185.

Gower et al., "Sterile shunt malfunction" J. Neurosurgery (1984) 61:1079–1084.

Holodny et al., "Focal dilation and paradoxical collapse of cortical fissures and suici in patients with normal–pressure hydrocephalus" J. Neurosurg. (1998) 89:742–747.

Kaye et al., "Plasticity in the aging brain" Arch Neurol. (1990) 47:1336–1341.

Langfitt, "Clinical methods for monitoring intracranial pressure and measuring cerebral blood flow" Clinical Neurosurgery, Proceedings of the Congress of Neurological Surgeons, Vancouver, British Columbia, The Williams & Wilkins Company, Baltimore, MD (1975) 22:302–320.

Magneas, "Body position and cerebrospinal fluid pressure" J. Neurosurgery (1976) 44:698–705.

Mogilner et al., "Hydrocephalus: Does coexistent Alzheimer's disease affect outcome" Poster Presentation from AANS 1999 New Orleans, http://cnshome.org/abstracts, 2 pages total.

ORBIS–Sigma® Valve Unit, Nitinol Medical Technologies, Inc. Boston, MA 02210 (formerly Cordis).

Williams et al., "Comparison of Pscf monitoring and controlled CSF drainage diagnose normal pressure hydrocephalus" Acta Neurochir. (1998) 71:326–330.

Wood, editor, "Body position and CSF pressure" Chapter 39, Neorobiology of Cerebrospinal Fouid 2, Plenum Press, New York, pp. 630–642.

Product Brochure for "The Future of CSF Shunting. The Phoenix Diamond™ Valve" Phoenix Corp., P.O. Box 80390, Valley Forge, PA 19426 2 pages total.

Medco Forum "CSF flow regulation: The future of CSF shunting" (Apr. 1998) vol. 3, 2 pages total.

Adams et al., "Disturbances of cerebrospinal fluid circulation, including hydrocephalus and meningeal reactions," Principles of Neurology, Fourth Edition, Chapter 30, 1989, pp. 501–502.

Adams, R.D. et al., "Symptomatic occult hydrocephalus with 'normal' cerebrospinal–fluid pressure" The New England Journal of Medicine, vol. 273, No. 3, pp. 117–126 (Jul. 15, 1965).

Appenzeller et al., Treatment of parenchymatous degeneration of the brain by ventriculo–atrial shunting of the cerebrospinal fluid, Journal of Neurosurgery, vol. XXVI, pp. 478–482, (Jan.–Jun. 1967).

Arai et al., "Tau in cerebrospinal fluid: a potential diagnostic marker," Ann. Neurology, vol. 38, 1995, pp. 649–652.

Bannister et al., "Isotope encephalography in the diagnosis of dementia due to communicating hydrocephalus" The Lancet, pp. 1014–1017, (Nov. 11, 1967).

Boon et al., "Dutch normal–pressure hydrocephalus study: Prediction of outcome after shunting by resistance to outflow of cerebrospinal fluid" J. Neurosurg. (1997) 87:687–693.

Bush et al., "Beta–A–4 amyloid protein and its precursor in Alzheimer's disease," Pharmac. Tera., vol. 56, 1992, pp. 97–117.

Chen, I.H. et al., "Effectiveness of shunting in patients with normal pressure hydrocephalus predicted by temporary, controlled-resistance, continuous lumbar drainage: a pilot study," *Journal of Neurology, Neurosurgery, and Psychiatry*, 1994, S/1430–1432.

Clarfield, "Normal-pressure hydrocephalus: Saga or swamp?" *JAMA* (1989) 262(18):2592–2593.

Committee on Medical Rating of Physical Impairment (McKeown, Raymond M. et al.,) The Central Nervous System, *JAMA*, "The Journal" Fifth in a series pp. 24–35 (Jul. 6, 1963).

Frankel et al., "High affinity binding of monoclonal antibodies to the sequential epitope EFRH of 9-amyloid peptide is essential for modulation of fibrillar aggregation" J. Immunol. (1999) 95:136–142.

Frankel et al., "Modulation of Alzheimer's ỹ-amyloid neurotoxicity by site-directed single-chain antibody" J. Immunol. (2000) 106:23–31.

Friedland, "Normal-pressure hydrocephalus and the saga of the treatable dementias" *JAMA* (1989) 262(18):2577–2581.

Golomb et al., "Alzheimer's disease comorbidity in normal pressure hydrocephalus: prevalence and shunt response" *J. Neurol. Neurosurg. Psych.* (2000) 66:778–781.

Graff-Radford et al., "Normal-pressure hydrocephalus" *Neurol.* (1986) 43:940–942.

Gustafson et al., "Recovery in hydrocephalic dementia after shunt operation" *J. Neurol Neurosurg. Psych.* (1978) 41:940–947.

Hakim et al., "The special clinical problem of symptomatic hydrocephalus with normal cerebrospinal fluid pressure. Observations on cerebrospinal fluid hydrodynamics" *J. Neurol. Sci.* (1965) 2:307–327.

Ko et al., "Cerebrospinal fluid control system" Proceedings of the IEEE, vol. 76, No. 9, pp. 1226–1235, Sep. 1988.

Martinez et al., "Relationship of interleukin-1 beta and beta$_2$-microglobulin with neuropeptides in cerebrospinal fluid of patients with dementia of the Alzheimer type," *J. Neuroimmunology*, vol. 48, 1993, pp 235–240.

Mataró et al., "Cognitive changes after cerebrospinal fluid shunting in young adults with spina bifida and assumed arrested hydrocephalus" *J. Neurol. Neurosurg. Psych.* (2000) 68:615–621.

Nakamura et al., "Amyloid beta protein levels in cerebrospinal fluid are elevated in early-onset Alzheimer's disease," *Ann. Neurology*, vol. 36, 1994, pp. 903–911.

Ono et al., "Formation of amyloid-like substance from beta-2-microglobulin in vitro. Role of serum amyloid P component: a preliminary study," *Nephron.* vol. 66, 1994, pp. 404–407.

Salmon, James H., "Senile and presenile dementia" *Geriatrics* (Dec. 1969) 24 (12): 67–72.

Shenkin et al., "Ventricular shunting for relief of senile symptoms" *JAMA* (1973) 225(12):1486–1489.

Skinhj, Erik, "Determination of regional cerebral bloodflow in man" Head injury conference proceedings, held at the University of Chicago Center for Continuing Education with Joseph P. Evans as host. No. 34, pp. 431–438.

Solomon et al., "Disaggregation of Alzheimer ỹ -amyloid by site-directed mAb" Proc. Natl. Acad. Sci. (1997) 94:4109–4112.

Solomon et al., "Monoclonal antibodies inhibit in vitr o bibrillar aggregation of the Alzheimer ỹ-amyloid peptide" Proc. natl. Acad. Sci. (1996) 93:452–455.

Vanneste et al., "Shunting normal-pressure hyrocephalus: Do the benefits outweigh the risks?" *Neurol.* (1992) 42:54–59.

Vorstrup et al., "Cerebral blod flow in patients with normal-pressure hydrocephalus before and after shunting" *J. Neurol.* (1987) 66:379–387.

Williams et al., "Evaluation of shunt function in patients who are never better, or better than worse after shunt surgery for NPH" *Acta Neurochir.* (1996) 71:368–370.

DEVICES AND METHODS FOR REMOVING CEREBROSPINAL FLUIDS FROM A PATIENT'S CSF SPACE

CROSS-REFERENCES TO ELATED APPLICATIONS

This application is a continuation of application Ser. No. 10/138,082, filed on May 3, 2002, now U.S. Pat. No. 6,575,928 which was a continuation of application Ser. No. 09/189,037, filed on Nov. 10, 1998, now U.S. Pat. No. 6,383,159, which issued on May 7, 2002, the full disclosures of which are incorporated herein.

BACKGROUND OF THE INVENTION

1. Field of the Invention

The present invention relates generally to medical devices and methods. More particularly, the present invention relates to improved devices and methods for removing cerebrospinal fluid (CSF) from the CSF space of a patient to treat Alzheimer's disease and other diseases.

Alzheimer's disease is a degenerative brain disorder which is characterized clinically by progressive loss of memory, cognition, reasoning, judgment, and emotional stability and which gradually leads to profound mental deterioration and ultimately death. Alzheimer disease is the most common cause of progressive mental failure (dementia) in aged humans and is estimated to represent the fourth most common medical cause of death in the United States. Alzheimer's disease has been observed in all races and ethnic groups worldwide and presents a major current and future public health problem. The disease is currently estimated to affect about two to four million individuals in the United States alone and is presently considered to be incurable.

Recently, a promising treatment for Alzheimer's disease has been proposed. The proposed treatment relies on the removal of cerebrospinal fluid (CSF) from the CSF space (which includes the subarachnoid space, the ventricles, the vertebral column, and the brain interstitial space) of a patient suffering from Alzheimer's disease. The treatment is based on the principle that in at least some cases, the characteristic lesions, referred to as senile (or amyloid) plaque and other characteristic lesions in the brain associated with Alzheimer's disease result from the retention of certain toxic substances in the CSF of the patient. A number of suspected pathogenic substances, including toxic, neurotoxic, and pathogenic substances, have been identified to date, including 1-amyloid peptide (Aâ-42 amyloid), MAP, tau, and the like. It is believed that freshly produced CSF has lower levels or is free of these toxic substances. Thus, it is believed that removal of CSF from the patient's CSF space will reduce the concentration of such substances and significantly forestall the onset and/or progression of Alzheimer's disease. This treatment for Alzheimer's disease has recently been described in Rubenstein (1998) *The Lancet,* 351:283–285, and published PCT application WO 98/02202.

Hydrocephalus is another condition which is treated by removing CSF from a patient's CSF space, in particular from the cerebral ventricles. Hydrocephalus is characterized by an elevated intracranial pressure resulting from excessive production or retention of CSF, and the removal of such excess CSF has been found to be a highly effective treatment for the condition. Numerous specific catheters and shunts have been designed and produced for the treatment of hydrocephalus, occult hydrocephalus, and other CSF disorders.

The removal of CSF for the treatment of either Alzheimer's disease or hydrocephalus can be accomplished using a wide variety of apparatus which are capable of collecting CSF in the CSF space, preferably from the intracranial ventricles, and transporting the collected fluid to a location outside of the CSF space. Usually, the location will be an internal body location, such as the venous system or the peritoneal cavity, which is capable of harmlessly receiving the fluid and any toxic substances, but it is also possible to externally dispose of the CSF using a transcutaneous device. An exemplary system for removing CSF from a patient's CSF space is illustrated in FIG. 1 and includes an access component 12, a disposal component 14, and a flow control component 16.

While the system of FIG. 1 in general will be suitable for the treatment of both Alzheimer's disease and hydrocephalus, specific characteristics of the flow control component should be quite different because of the different nature of the two diseases. Treatment of hydrocephalus is best accomplished by controlling the flow rate of CSF from the CSF space to the disposal location in order to maintain intracranial pressure within normal physiological limits. Particularly suitable flow control characteristics for a flow control module in a hydrocephalus treatment system are illustrated in FIG. 2. FIG. 2 is taken from U.S. Pat. No. 4,781,672 which describes a flow control valve of the type used in the commercially available Orbis-Sigma® valve unit available from Nitinol Medical Technologies, Inc. Boston, Mass., 02210 (formerly from Cordis, Miami, Fla.). Briefly, the pressure P is the differential pressure between the CSF space and the disposal location. The patent teaches that the control valve establishes an initial flow rate Q1 of about 0.4 ml/min when the differential pressure P reaches an initial level P1 of 80 mm $H_2O$ and increases to a higher flow rate Q2 of 0.8 ml/min as the differential pressure increases to a higher value P2 of 350 mm $H_2O$. When pressure P is below P1, there is essentially no flow. At pressures above P2, the flow is essentially unrestricted. Such valve flow characteristic are particularly suitable for treating hydrocephalus because for pressures below P1, there is no need to reduce pressure and thus no need to remove CSF. For pressures from P1 to P2, a controlled removal of CSF is desired to lower intracranial pressure with minimum risk of removing excessive amounts of CSF. When intracranial pressure exceeds P2 rapid removal of CSF is necessary to immediately lower intracranial pressure to a safer level. Such previous systems for draining CSF from the CSF space of the patient are generally not suitable for the treatment of patients suffering from Alzheimer's disease or other conditions relating to toxic substances in the CSF.

For these reasons, it would be desirable to provide devices and methods for removing CSF from the CSF space of a patient, where such devices and methods are particularly modified and optimized for treating Alzheimer's disease and other conditions relating to toxic substances in cerebrospinal fluid. Such devices and methods will preferably provide for the controlled removal of CSF from the patient in a manner which effectively removes the toxic substances to reduced levels without excessive removal of the CSF in a manner which places the patient at risk. Such objective will be met at least in part by the invention described hereinafter.

2. Description of Background Art

The treatment of Alzheimer's disease by removing cerebrospinal fluid from the CSF region of the brain is described in co-pending applications U.S. Ser. No. 08/678,191, filed on Jul. 11, 1996, and U.S. Ser. No. 08/901,023, filed on Jul. 25, 1997, both of which are assigned to the assignee of the present invention. The full disclosures of each of these two applications are incorporated herein by reference. The latter application is equivalent to WO 98/02202.

Methods and shunts for treating hydrocephalus are described in U.S. Pat. Nos. 3,889,687; 3,985,140; 3,913,587; 4,375,816; 4,377,169; 4,385,636; 4,432,853; 4,532,932; 4,540,400; 4,551,128; 4,557,721; 4,576,035; 4,595,390; 4,598,579; 4,601,721; 4,627,832; 4,631,051; 4,675,003; 4,676,772; 4,681,559; 4,705,499; 4,714,458; 4,714,459; 4,769,002; 4,776,838; 4,781,672; 4,787,886; 4,850,955; 4,861,331; 4,867,740; 4,931,039; 4,950,232; 5,039,511; 5,069,663; 5,336,166; 5,368,556; 5,385,541; 5,387,188; 5,437,627; 5,458,606; PCT Publication WO 96/28200; European Publication 421558; 798011; and 798012; French Publication 2 705 574; Swedish Publication 8801516; and SU 1297870. A comparison of the pressure-flow performance of a number of commercially available hydrocephalus shunt devices is presented in Czosnyka et al. (1998) *Neurosurgery* 42: 327–334. A shunt valve having a three-stage pressure response profile is sold under the Orbis-Sigma® tradename by Nitinol Medical Technologies, Inc. Boston, Mass. 02210 (formerly by Cordis). U.S. Pat. No. 5,334,315, describes treatment of various body fluids, including cerebrospinal fluids, to remove pathogenic substances therefrom.

Articles discussing pressures and other characteristics of CSF in the CSF space include Condon (1986) *J. Comput. Assit. Tomogr.* 10:784–792; Condon (1987) J. Comput. Assit. Tomogr. 11:203–207'; Chapman (1990) *Neurosurgery* 26:181–189; Magneas (1976) *J Neurosurgery* 44:698–705; Langfitt (1975) *Neurosurgery* 22:302–320.

BRIEF SUMMARY OF THE INVENTION

Devices and methods according to the present invention provide for the controlled and optimized removal of cerebrospinal fluid (CSF) from the CSF space of a patient. The devices and methods are particularly intended for the treatment of Alzheimer's disease and other conditions which are caused by or otherwise related to the retention and accumulation of toxic substances in the CSF. In addition to Alzheimer's disease, the present invention will be useful for treating other conditions resulting from the accumulation of toxic substances and resulting lesions in the patient's brain, such as Down's Syndrome, hereditary cerebral hemorrhage with amyloidosis of the Dutch-Type (HCHWA-D), and the like. Other treatable conditions relating to the chronic or acute presence of potentially putative substances include epilepsy, narcolepsy, Parkinson's disease, polyneuropathies, multiple sclerosis, amyotrophic lateral sclerosis (ALS), myasthenia gravis, muscular dystrophy, dystrophy myotonic, other myotonic syndromes, polymyositis, dermatomyositis, brain tumors, Guillain-Barre-Syndrome, and the like.

Devices and methods of the present invention are intended for treating conditions in patients having "normal" intracranial pressures, i.e. intracranial pressures below 200 mm $H_2O$ when the patient is reclining and above −170 mm $H_2O$ when the patient is upright (where the pressures are measured relative to the ambient). In contrast, patients suffering from hydrocephalus will have constant or periodic elevated intracranial pressures above 200 mm $H_2O$ (when reclining), often attaining levels two or three times the normal level if untreated. The devices and methods of the present invention are not intended for the treatment of patients having elevated intracranial pressures in general and patients suffering from hydrocephalus in particular.

The differences in untreated intracranial and ventricular pressures as well as the different treatment end points (the treatment of hydrocephalus requires lowering of elevated pressures while treatments according to present inventions require lowering of the concentrations of substances in the CSF) require significantly different treatment devices and methods. In particular, treatments and methods according to present invention rely on relatively low CSF removal rates, usually in the range from 0.01 ml/min to 0.2 ml/min, more usually in the range from 0.03 ml/min to 0.1 ml/min, and preferably in the range from 0.04 ml/min to 0.06 ml/min. Further preferably, CSF removal at such low rates will occur continuously or at least so long as the intracranial and ventricular pressures do not fall below certain minimal levels, e.g. below about −170 mm $H_2O$. Such safety thresholds correspond generally to the lowest expected ventricular pressure of the patient when upright. The intracranial and ventricular pressures referred to above are defined or measured as "gauge" pressures, i.e. relative to ambient. The intracranial pressure falls below ambient (0 mm$H_2O$) as a result of the compliant nature of the CSF space and the column of CSF fluid which is created as the patient sits upright or stands. The ability of the flow control module to maintain a relatively constant flow (as defined below) regardless of the variations in the intracranial or ventricular "source" pressure is an important aspect of the present invention.

The CSF removal techniques of the present invention generally rely on pressure-compensated removal to achieve the desired constant flow rate, where the generally constant (usually varying by no more than ±75%, preferably no more than ±50%, and more preferably ±20%) removal rate is achieved by providing a pressure-controlled variable resistance path in the flow control module between the CSF space and the disposal site. In contrast, the flow control valves for hydrocephalus treatment, such as those described in U.S. Pat. No. 4,781,672, intentionally provide for significant variation in flow rate as the pressure differential across the flow valve passes through specific control points. Use by the present invention of a generally constant flow rate which is below the normal CSF production rate minimizes the possibility of over removal of the CSF and the risk of occlusion associated with CSF stagnation. In a first aspect, methods for reducing the concentrations of toxic substances in CSF comprise establishing a drain path from a CSF space in the patient, typically a ventricle in the brain. The drain path is configured or defined to remove CSF at a rate in the ranges set forth above while the intracranial pressure may vary over a relatively broad range, typically from −170 mm $H_2O$ to 200 mm $H_2O$, depending on patient orientation. Usually, the CSF flow rate will vary by no more than ±75%, usually ±50%, and preferably ±20%, as the intracranial pressure varies over the above range.

The drain path may extend to any internal or external disposal location of a type commonly used with the treatment of hydrocephalus. Usually, the disposal location will be into the venous system, the peritoneal cavity (peritoneal space), the pleural cavity (pleural space), or the like. It will also be possible (although usually less desirable) to employ transcutaneous devices where disposal occurs to an external space outside of the patient's body, e.g. into a drainage bag.

Apparatus according to present invention comprise access component, such as a catheter adapted to reside in the ventricle or other portion of the CSF space of the patient, (e.g., a lumbar space) and a flow control component connectable to an outlet of the access component. The flow control component will be adapted to control the CSF flow rate from the access component within the flow rate ranges set forth above, while the pressure in the CSF space varies over the range set forth above. In the illustrated embodiments, the flow control component will be passive, i.e. a pressure-compensated flow control valve. The present invention, however, also includes actively controlled flow control valves and pumps, where the valves and pumps can be powered by battery, patient movement, or the like. The apparatus may further comprise a disposal component connectable to an outlet of the flow control component. The disposal component will usually be adapted to further direct the drain path to a target disposal site, such as the venous system, peritoneal cavity, pleural cavity, or the like. Preferably, the flow control component will further be adapted to stop or greatly reduce the flow of CSF when intracranial pressure falls below the safety threshold set forth above.

In some instances, the apparatus may comprise the flow control module alone.

In a specific embodiment, the flow control module according to the present invention comprises a diaphragm valve connectable to an outlet of an access component. The diaphragm valve includes a pressure-responsive diaphragm, a contoured plug, and an orifice which receives the contoured plug and permits the flow of CSF therethrough. Either the plug or the orifice is coupled to move with the diaphragm in response to changes in the differential pressure across the valve. The contoured plug has a profile (or other modification) which is selected to provide a variable annular flow region between the plug and the orifice so that flow is controlled within the target range as set forth above while the intracranial pressure varies within the range set forth above. Usually, the orifice will be directly coupled to the diaphragm, while the plug is fixed relative to a valve body. The apparatus may further comprise an access component and/or a disposal component, which may be any of the components described above.

DETAILED DESCRIPTION OF THE INVENTION

Figure 1:
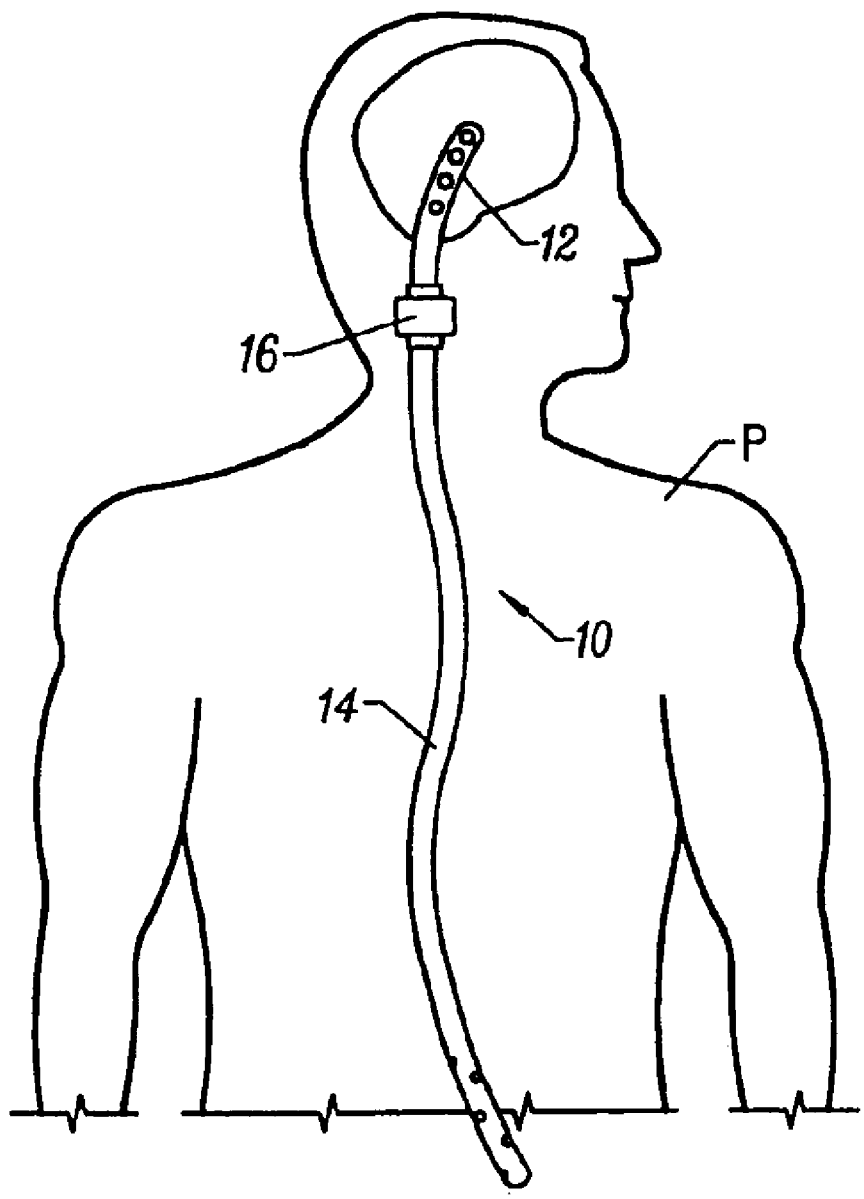
FIG. 1 is a schematic illustration showing the components and placement of a conventional system for removing cerebrospinal fluid from a CSF space of the brain.
Figure 1A:
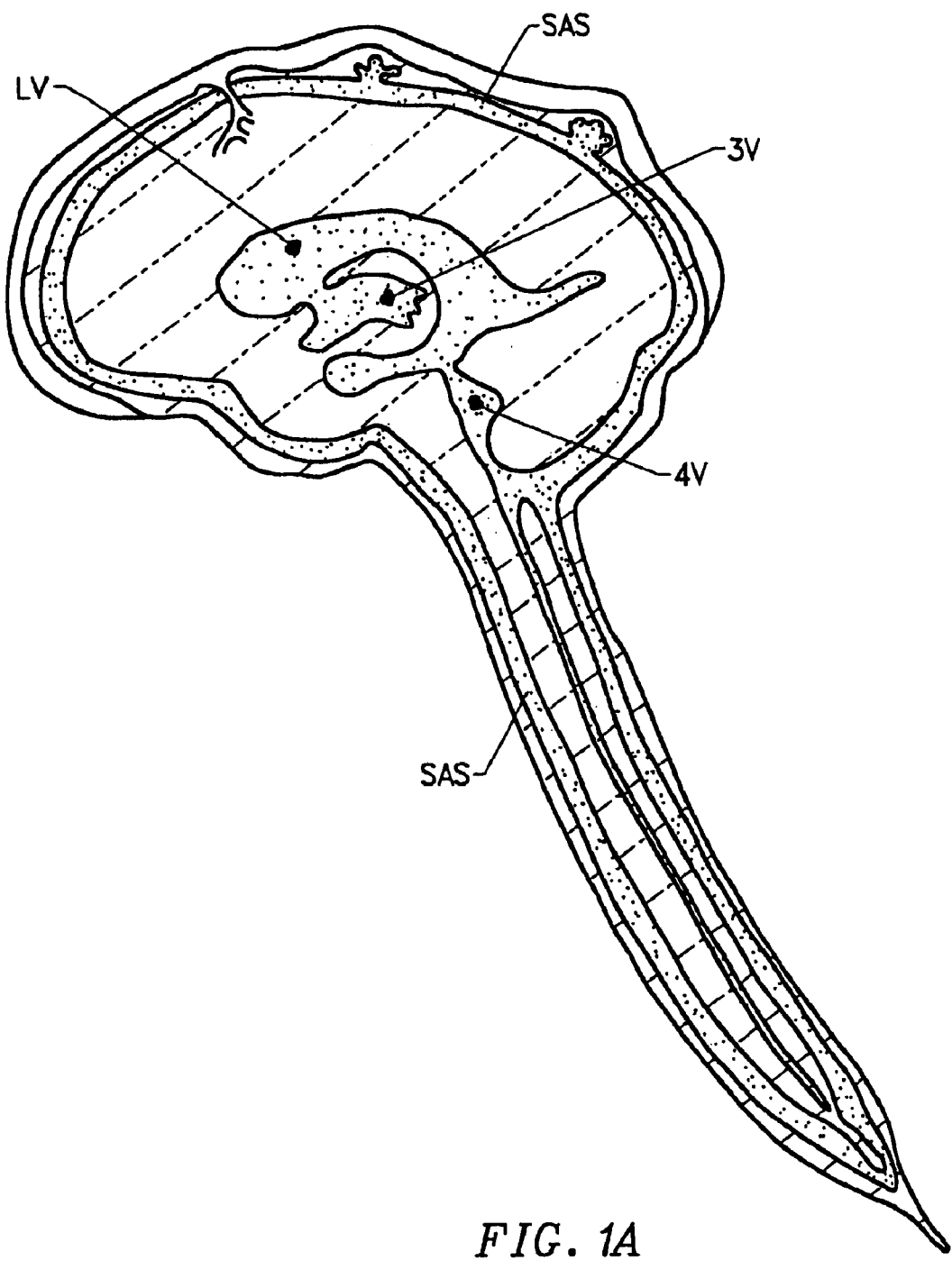
Figure 2:
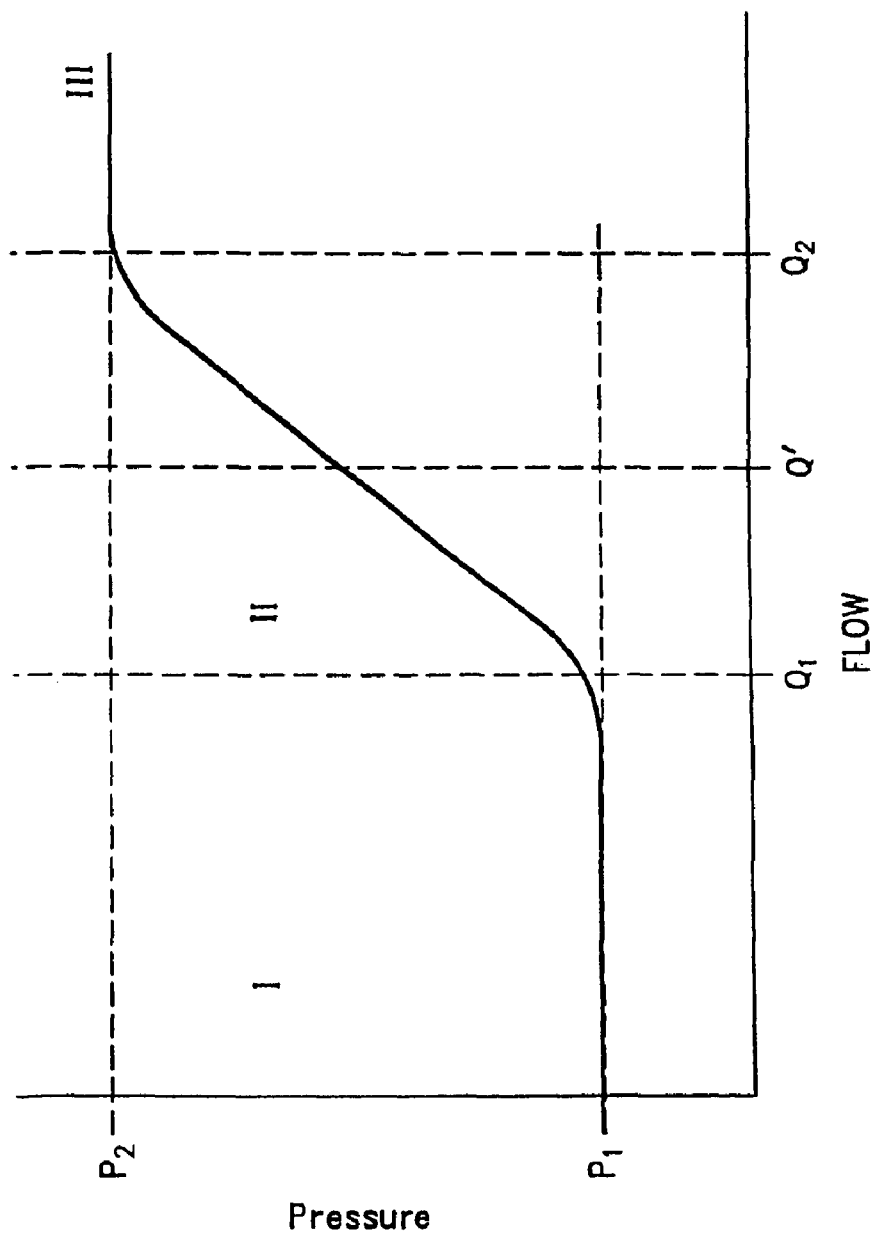
FIG. 2 illustrates the pressured-flow relationship of a conventional flow valve used in systems such as those shown in FIG. 1 for treating hydrocephalus.

The brain and spinal cord are bathed in cerebrospinal fluid (CSF) and encased within the cranium and vertebral column inside a thin membrane known as the meninges (FIG. 1A). The space within the meninges includes the subarachnoid space SAS, the ventricles (including the lateral ventricle LV, third ventricle 3V, and fourth ventricle 4V), the vertebral column, and the brain interstitial spaces, and is referred to herein as the "CSF space." The volume of the brain intracranial spaces is on average about 1700 ml. The volume of the brain is approximately 1400 ml, and the volume of the intracranial blood is approximately 150 ml. The remaining 150 ml is filled with CSF (this volume may vary within 60 ml to 290 ml). The CSF circulates within the CSF space. CSF is formed principally by the choroid plexuses, which secrete about 80% of the total volume of the CSF. The sources of the remainder are the vasculature of the subependymal regions, and the pia matter. The total volume of the CSF is renewed several times per day, so that about 500 ml are produced every 24 hours (equivalent to about 20 ml/hr or 0.35 ml/min) in healthy adults. The production rate varies in the old and the young.

The cerebrospinal fluid is absorbed through the arachnoid villi, located principally over the superior surfaces of the cerebral hemispheres. Some villi also exist at the base of the brain and along the roots of the spinal nerves. The absorptive processes include bulk transport of large molecules and as well as diffusion across porous membranes of small molecules. The production and absorption of CSF are well described in the medical literature. See, e.g., Adams et al. (1989) "Principles of Neurology," pp. 501–502.

While CSF is naturally absorbed and removed from circulation, as just described, it is presently believed that certain toxic substances which may be present in the CSF, such as those associated with Alzheimer's disease, may accumulate or persist to an extent which can cause Alzheimer's disease or other disorders. Such substances are either produced in excess and/or are removed at a rate slower than their production rate so that they accumulate and increase in toxicity and/or reach a threshold concentration in which they become toxic in the brain or elsewhere within CSF space. The present invention is directed at particular devices and methods for the improved removal of such substances from the CSF in order to treat, inhibit, or ameliorate conditions associated with such toxic materials. In particular, the present invention is directed at reducing the concentration of such substances in CSF by removing portions of the CSF from the CSF space. Such removal is believed to either enhance production of the CSF and/or reduce the natural absorption of the CSF so that the total volume of CSF in the CSF space is not reduced below a safe level. Moreover, the rates at which the CSF is removed are generally quite low (when compared to the rates of removal for treatment of the hydrocephalus) so that the likelihood of removing excessive amounts of CSF is very low.

By removing CSF from the CSF space, the toxic substances present in the removed CSF will thus be removed from the CSF space and will not be available for absorption or recirculation. So long as the rate of removal exceeds the rate of production of such substances, the concentration of such substances can be reduced. Usually, the removed CSF will be directed to a natural disposal site within the patient's body which can tolerate the toxic substance. Suitable sites, particularly for those substances associated with Alzheimer's disease as discussed above, include the venous system, peritoneal cavity, the pleural cavity, and the like. In the event that a toxic substance would be deleterious if transferred within the patient's body, or for any other reason, it is also possible to remove the CSF from the patient's body, e.g. using a transcutaneous catheter and external collection bag or other receptacle. It will generally be preferable to maintain the entire system subcutaneously for patient convenience and to reduce the risk of infection.

Figure 3:
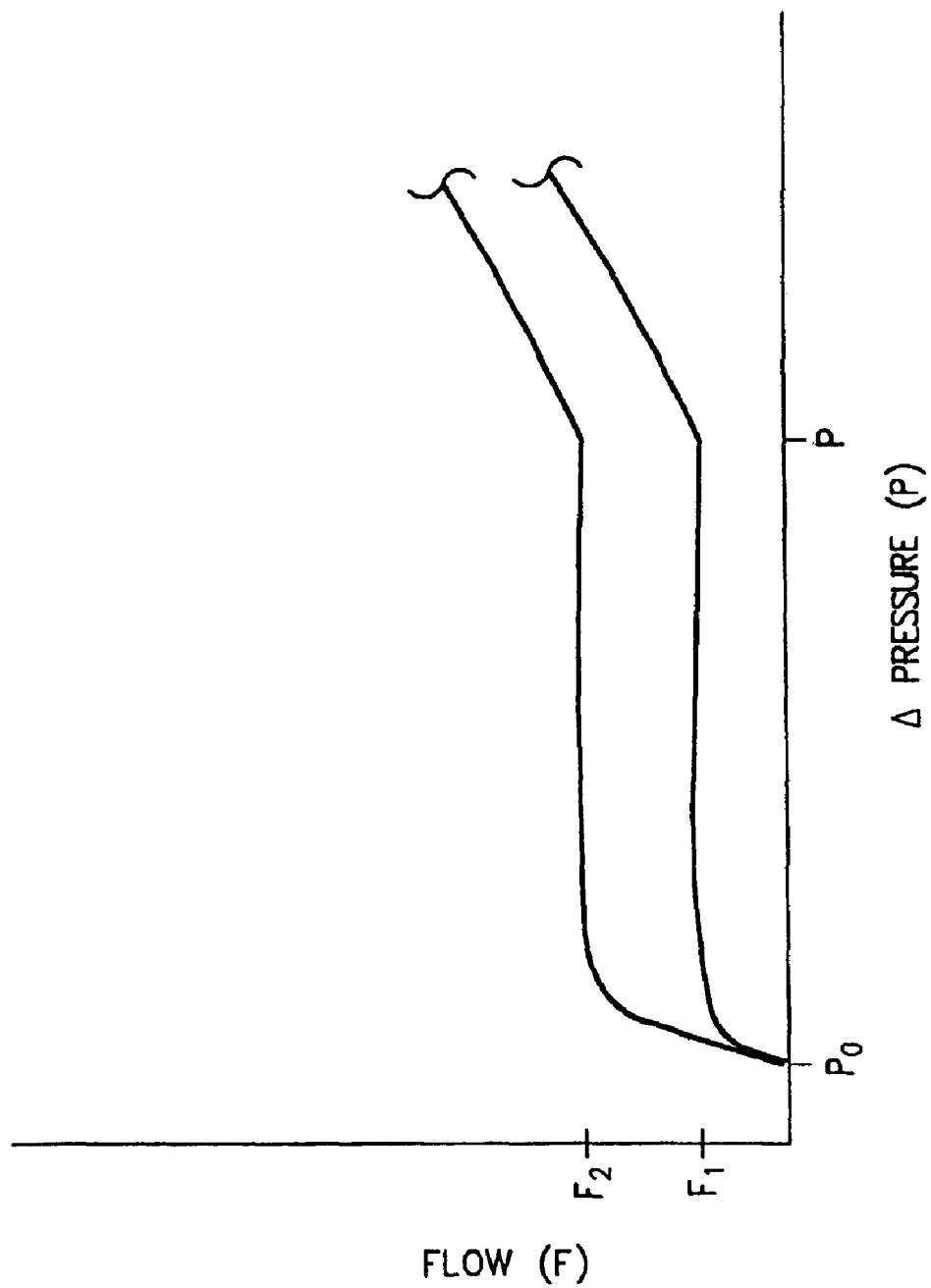
FIG. 3 illustrates exemplary flow-pressure relationships for the devices and methods of the present invention.

Referring to FIG. 3, the devices and methods of present inventions are particularly intended to maintain a relatively constant flow rate F of CSF from the CSF space at normal intracranial pressures P (e.g. −170 mm $H_2O$ to 200 mm $H_2O$ relative to ambient). For safety, the devices and methods will be configured to remove little or no CSF at intracranial pressures below a threshold value $P_0$ which is at or near the lowest expected intracranial pressure for an upright patient, typically −170 mm of $H_2O$. At intracranial pressures above $P_0$, the CSF flow rate F will usually be between a lower values $F_1$ and an upper value $F_2$, with particular ranges set forth above. Usually, the flow rate F will be at a relatively constant level, with the rate preferably being pressure-corrected so that it does not vary by more than ±75%, preferably by no more than ±50%, and more preferably by no more than ±20% for intracranial pressures within the expected ranges. As observed in FIG. 3, it is desirable that the flow rate F be constant at least over the range $P_0$ to $P_1$, and more preferable that the flow rate remains constant for even higher differential pressures since the present invention is not intended to treat excessive intracranial pressure, but rather to remove the CSF at a relatively low, constant rate regardless of the differential pressure (so long as P is above the threshold $P_0$).

Figure 4:
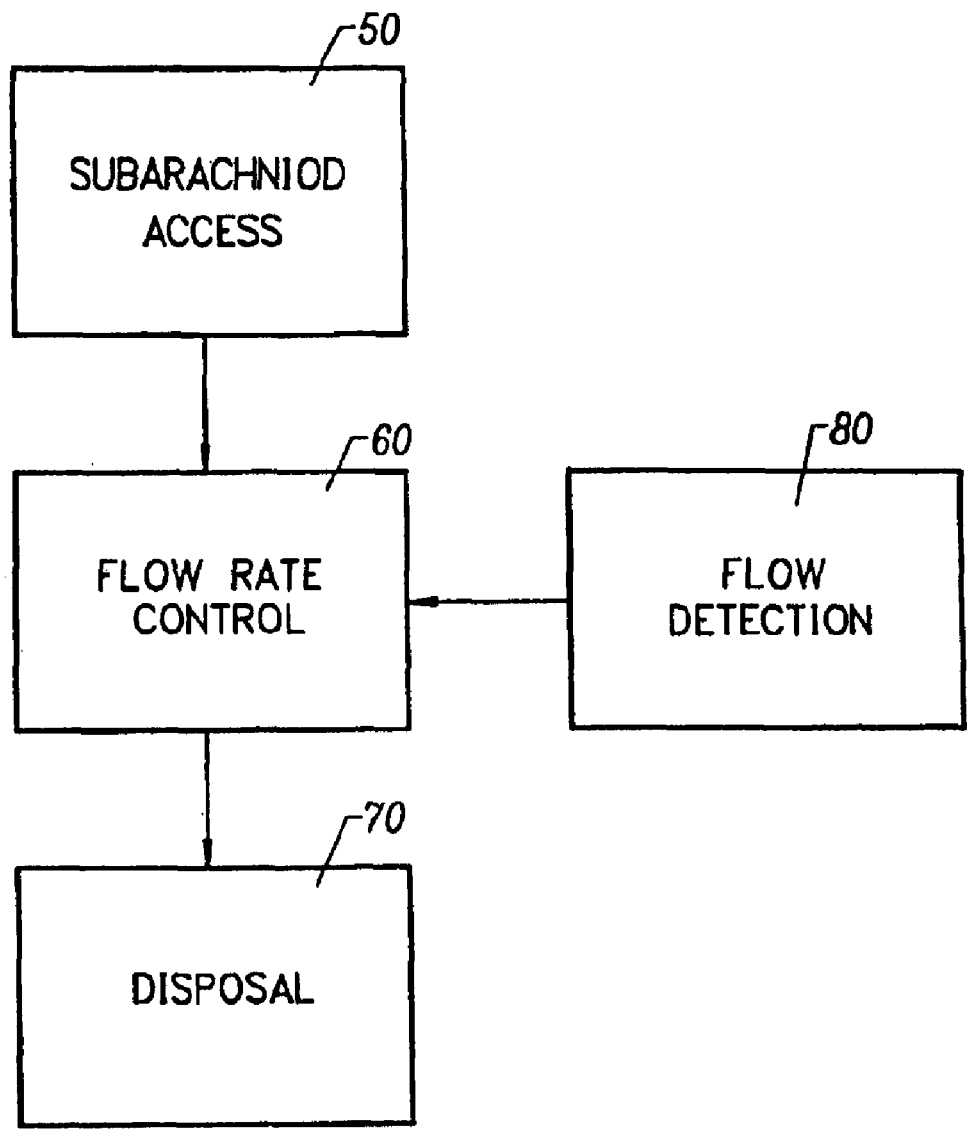
FIG. 4 is a schematic illustration of apparatus according to the present invention for draining CSF from a CSF space of the patient's brain in accordance with the principles of the present invention.

Apparatus according to the present invention for removing CSF from a CSF space is illustrated schematically in FIG. 4. Apparatus will generally include an access component 50, a flow rate control component 60, optionally a disposal component 70, and optionally a flow or detection component 80. With the exception of the flow rate control component 60, present invention may use components of a type described in co-pending application Serial No. 08/901,023, the full disclosure which has previously been incorporated herein by reference. The flow rate control component 60, however, will be constructed specifically to achieve the flow-pressure response characteristics which have been discussed previously.

Figure 5A:
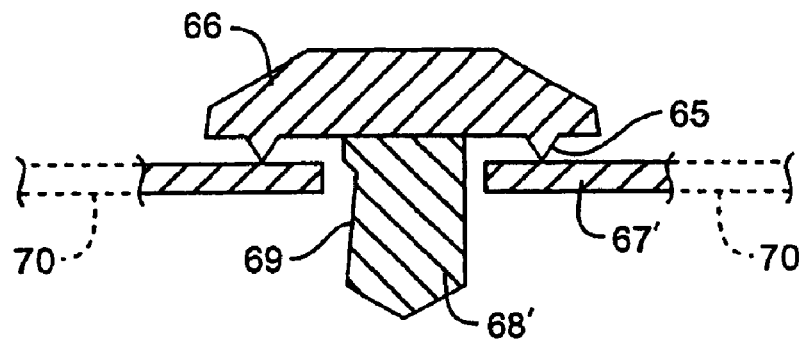
FIGS. 5A–5C illustrates modifications that can be made to the flow control valve of U.S. Pat. No. 4,781,672, so that the valve described in that patent will display flow-pressure characteristics in accordance with the principles of the present invention.
Figure 5B:
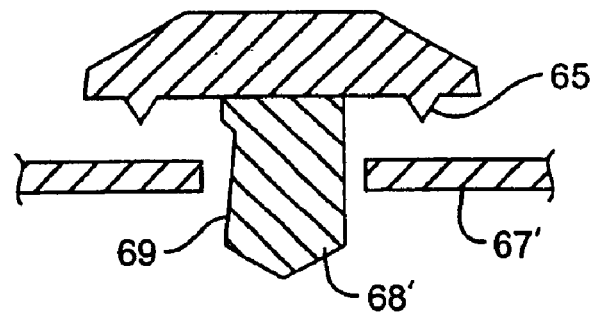
Figure 5C:
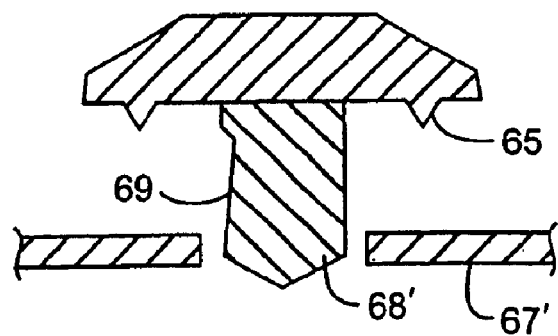

As illustrated in FIGS. 5A–5C, a passive flow control valve of the type illustrated in U.S. Pat. No. 4,781,672, may be modified to provide the flow-pressure characteristics of the present invention. The full disclosure of U.S. Pat. No. 4,781,672, is incorporated herein by reference. By modifying the characteristics of valve seat 67 and valve stem 68 (and optionally the diaphragm and/or other valve components) in that patent, the flow characteristic of the present invention may be achieved. In particular, by substituting valve seat 67' and valve stem 68', as illustrated in FIGS. 5A–5C the desired flow characteristics can be achieved. The valve seat 67' and valve stem 68' comprise an orifice and contoured valve plug according to the claims in the present application. A notched, sliced or tapered surface 69 maybe formed on one side of the valve plug 68' to change the available annular area between the plug and the seat 67' as the plug is raised relative to the seat, as shown in FIGS. 5B and 5C. When the valve structure is closed, as shown in FIG. 5A, an annular ring 65 formed on the lower surface of a stationary component 66 seats against an upper surface of the valve seat 67'. Thus, the valve is closed. As CSF flows into the valve structure, it exerts pressure against the valve seat 67', which is mounted in a diaphragm 70 (shown in broken line in FIG. 5A) causing the valve seat to move lower as shown in both FIGS. 5B and 5C. With a relatively low differential pressure, the valve seat 67' lowers partly down the valve plug 68', entering into or further a portion of the notched region 69 which expands the annular space between the plug 68' and the valve seat 67'. As the inlet pressure further increases (and thus the differential pressure also increases), the valve seat 67' moves further down, moving to a portion of the notch where the available flow area through the valve seat 67' is reduced. Thus, the valve structure is pressure-compensated so that the resistance to flow increases as the differential pressure increases, which acts to maintain a constant flow rate regardless of the system differential pressure. The total travel of the valve from FIG. 5A–5C will generally be selected to occur so that the valve first opens at a differential pressure of approximately $P_0$ and fully opens at a differential pressure which is well above the maximum expected differential pressure P, so that relatively constant flow rates may be maintained over the entire expected differential pressure range $P_0$ to $P_1$. In all cases, the values P of differential pressure are the sum of the intracranial pressure, hydrostatic pressure, and pressure at the release site, e.g. intra-abdominal pressure.

Figure 6A:
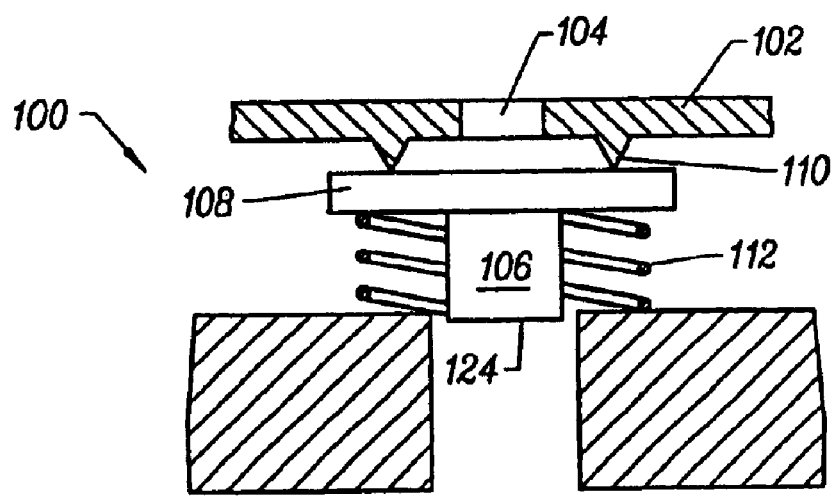
FIGS. 6A and 6B illustrate an alternative embodiment of a valve mechanism for practicing the present invention.
Figure 6B:
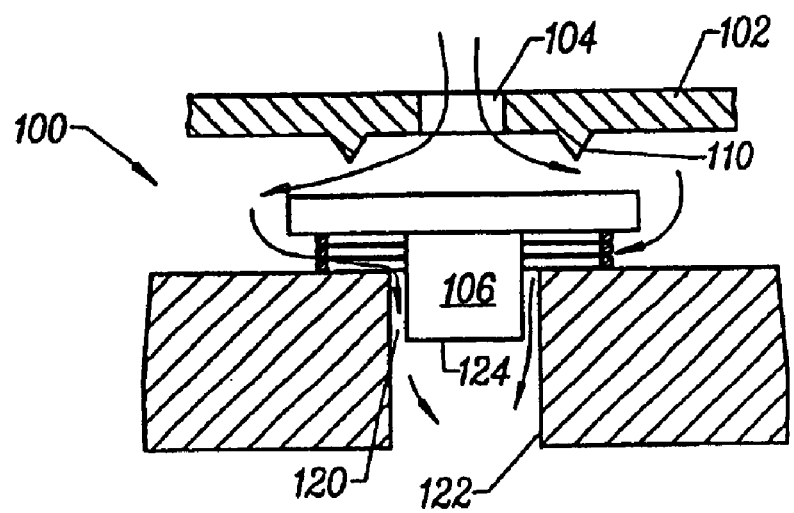

While modification of the commercially available Orbis-Sigma® valve units will be particularly convenient, a wide variety of other specific valve designs will also be available to provide the desired pressure-flow characteristics of the present invention. Referring now two FIGS. 6A and 6B, a valve structure 100 comprises a plate 102 having an inlet orifice 104. A reciprocating valve plug 106 is attached to the plate 108 on its upper end. The plate seats against a sealing ring 110 projecting downwardly from the plate 102 so that the valve is closed until a sufficient CSF inlet pressure develops across orifice 104 to open valve plug 106 against a spring 112 which is under slight compression. Once the valve is opened, as shown in FIG. 6B, CSF will flow past the plate 108 and into the annular space 120 between the plug 106 and a cylindrical wall 122 formed in the valve body. As the inlet pressure and the differential pressure increase, the plug 20 will be further lowered, thus increasing the length of the annular lumen which is formed between the plug 106 and the cylindrical wall 122. As the lumen length further increases, the resistance to flow also increases, thus making the valve structure 100 a pressure-compensating structure in accordance with the principles of the present invention. That is, as the differential pressure across the plug 106 increases, the plug will be displaced further into the cylindrical space 122. A force balance will be reached when the upward force of spring 112 becomes equal the downward force on the plug 106 by the differential pressure across the plug. The valve plug will thus move downward to increase flow resistance in response to increased differential pressures.

A wide variety of other particular valve structures are also available.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for reducing the level of toxic substances in cerebrospinal fluid (CSF) of a patient, said method comprising:

identifying a patient suffering from a condition related to the retention and accumulation of toxic substances in the CSF and having normal intracranial pressure below 200 mm $H_2O$ when reclining and above −170 when upright; and establishing a drain path from a CSF space of the patient, wherein said drain path will remove CSF at a rate in the range from 0.01 ml/minute to 0.2 ml/minute while pressure in the subarachnoid space varies over the entire normal range from −170 mm $H_2O$ to 200 mm $H_2O$.

2. A method as in claim 1, wherein the drain path will remove CSF at a rate in the range from 0.03 ml/minute to 0.1 ml/minute over said pressure range.

3. A method as in claim 2, wherein the drain path will remove CSF at a rate in the range from 0.04 ml/minute to 0.06 ml/minute over said pressure range.

4. A method as in claim 1, wherein the CSF flow rate varies by no more than ±75% as the CSF space pressure varies over said range.

5. A method as in claim 1, wherein the drain path extends into a peritoneal space, a pleural space, the venous system, or an external space.

6. A method as in claim 1, wherein the CSF flow rate varies by no more than ±50% as the CSF space pressure varies over said range.

7. A method as in claim 1, wherein the CSF flow rate varies by no more than ±20% as the CSF space pressure varies over said range.

8. A method as in claim 1, wherein the drain path will stop the flow of CSF from the subarachnoid region when pressure in the CSF space falls below −170 mm $H_2O$.

9. A method as in claim 1, wherein the patient suffers from a disease selected from the group consisting of Alzheimer's disease, Down's Syndrome, and HCHWA-D.

10. A method as in claim 1, wherein establishing comprises implanting a conduit between the CSF space to a drainage location, wherein said conduit comprises a flow control component adapted to control the CSF flow rate in the range from 0.01 ml/minute to 0.2 ml/minute while pressure in the CSF space varies from −170 mm $H_2O$ to 200 mm $H_2O$.

11. A method as in claim 10, wherein the flow control component is adapted to control the CSF flow at a rate in the range from 0.03 ml/minute to 0.1 ml/minute over said pressure range.

12. A method as in claim 10, wherein the flow control component is adapted to control the CSF flow from 0.04 ml/minute to 0.06 ml/minute over said pressure range.

13. A method as in claim 10, wherein the flow control component establishes a CSF flow rate which varies no more than ±75% in response to a CSF space pressure which varies over said range.

14. A method as in claim 10, wherein the flow control component establishes a CSF flow rate which varies by no more than ±50% in response to a CSF space pressure which varies over said range.

15. A method as in claim 10, wherein the flow control component establishes a CSF flow rate which varies by no more than ±20% in response to a CSF space pressure which varies over said range.

16. A method as in claim 1, further comprising stopping the flow of CSF from the CSF space when intracranial pressure falls below −170 mm $H_2O$.

17. A method for reducing the level of toxic substances in cerebrospinal fluid (CSF) of a patient, said method comprising:
identifying a patient suffering from Alzheimer's disease and having normal intracranial pressure below 200 mm $H_2O$ when reclining and above −170 when upright; and
establishing a drain path from a CSF space of the patient, wherein said drain path will remove CSF at a rate in the range from 0.01 ml/minute to 0.2 ml/minute while pressure in the subarachnoid space varies over the entire normal range from −170 mm $H_2O$ to 200 mm $H_2O$.

18. A method as in claim 17, wherein the drain path will remove CSF at a rate in the range from 0.03 ml/minute to 0.1 ml/minute over said pressure range.

19. A method as in claim 18, wherein the drain path will remove CSF at a rate in the range from 0.04 ml/minute to 0.06 ml/minute over said pressure range.

20. A method as in claim 17, wherein the CSF flow rate varies by no more than ±75% as the CSF space pressure varies over said range.

21. A method as in claim 17, wherein the drain path extends into a peritoneal space, a pleural space, the venous system, or an external space.

22. A method as in claim 17, wherein the CSF flow rate varies by no more than ±50% as the CSF space pressure varies over said range.

23. A method as in claim 17, wherein the CSF flow rate varies by no more than ±20% as the CSF space pressure varies over said range.

24. A method as in claim 17, wherein the drain path will stop the flow of CSF from the subarachnoid region when pressure in the CSF space falls below −170 mm $H_2O$.

25. A method as in claim 17, wherein establishing comprises implanting a conduit between the CSF space to a drainage location, wherein said conduit comprises a flow control component adapted to control the CSF flow rate in the range from 0.01 ml/minute to 0.2 ml/minute while pressure in the CSF space varies from −170 mm $H_2O$ to 200 mm $H_2O$.

26. A method as in claim 25, wherein the flow control component is adapted to control the CSF flow at a rate in the range from 0.03 ml/minute to 0.1 ml/minute over said pressure range.

27. A method as in claim 25, wherein the flow control component is adapted to control the CSF flow from 0.04 ml/minute to 0.06 ml/minute over said pressure range.

28. A method as in claim 25, wherein the flow control component establishes a CSF flow rate which varies no more than ±75% in response to a CSF space pressure which varies over said range.

29. A method as in claim 25, wherein the flow control component establishes a CSF flow rate which varies by no more than ±50% in response to a CSF space pressure which varies over said range.

30. A method as in claim 25, wherein the flow control component establishes a CSF flow rate which varies by no more than ±20% in response to a CSF space pressure which varies over said range.

31. A method as in claim 17, further comprising stopping the flow of CSF from the CSF space when intracranial pressure falls below −170 mm $H_2O$.

32. Apparatus for draining cerebrospinal fluid (CSF) from a CSF space of a patient, said apparatus comprising:
an access component having an inlet and an outlet; and
a flow control component connectable to the outlet of the access component to establish a drain path, wherein said flow control component is adapted to control the CSF flow rate in the range from 0.01 ml/minute to 0.2 ml/minute while pressure in the CSF space varies over the entire range from −170 mm $H_2O$ to 200 mm $H_2O$.

33. Apparatus as in claim 32, wherein the drain path is adapted to control the CSF flow at a rate in the range from 0.03 ml/minute to 0.1 ml/minute over said pressure range.

34. Apparatus as in claim 33, wherein the drain path is adapted to control the CSF flow from 0.04 ml/minute to 0.06 ml/minute over said pressure range.

35. Apparatus as in claim 32, wherein the flow control component establishes a CSF flow rate which varies no more than ±75% in response to a CSF space pressure which varies over said range.

36. Apparatus as in claim 32, wherein the flow control component establishes a CSF flow rate which varies by no more than ±50% in response to an CSF space pressure which varies over said range.

37. Apparatus as in claim 32, wherein the flow control component establishes a CSF flow rate which varies by no more than ±20% in response to an CSF space pressure which varies over said range.

38. Apparatus as in claim 32, further comprising a disposal component connectable to the flow control component.

39. Apparatus as in claim 32, wherein the flow control element will stop the flow of CSF from the CSF space when intracranial pressure falls below −170 mm $H_2O$.

40. Apparatus for draining cerebrospinal fluid (CSF) from a CSF space of a patient's brain, said apparatus comprising:

an access component having an inlet and an outlet; and a diaphragm valve connectable to the outlet of the access component and including a pressure-responsive diaphragm, a contoured plug, and an orifice which receives the contoured plug and permits the flow of CSF therethrough, wherein one of the plug and orifice is coupled to the diaphragm so that the plug and orifice will move reflective to each other in response to changes in pressure of CSF from the outlet of the access component against the diaphragm, wherein the contoured plug has a profile adapted to control the CSF flow rate through the orifice in the range from 0.01 ml/minute to 0.2 ml/minute while pressure in the CSF space varies over the entire range from −170 mm $H_2O$ to 200 mm $H_2O$.

41. Apparatus as in claim 40, wherein the orifice is coupled directly to the diaphragm.

42. Apparatus as in claim 40, further comprising a disposal component connectable to the diaphragm valve.

43. Apparatus as in claim 40, where the contoured plug profile is selected to remove CSF at a rate in the range from 0.03 ml/minute to 0.1 ml/minute over said pressure range.

* * * * *